(12) United States Patent
Desilets et al.

(10) Patent No.: US 7,905,844 B2
(45) Date of Patent: *Mar. 15, 2011

(54) DISPOSABLE TRANSDUCER SEAL

(75) Inventors: Charles S. Desilets, Edmonds, WA (US); George Barrett, Lake Forest Park, WA (US); Jens U. Quistgaard, Seattle, WA (US); Gregory Paul Darlington, Snohomoish, WA (US)

(73) Assignee: Medicis Technologies Corporation, Bothell, WA (US)

( * ) Notice: Subject to any disclaimer, the term of this patent is extended or adjusted under 35 U.S.C. 154(b) by 678 days.

This patent is subject to a terminal disclaimer.

(21) Appl. No.: 11/935,481

(22) Filed: Nov. 6, 2007

(65) Prior Publication Data

US 2008/0064961 A1    Mar. 13, 2008

Related U.S. Application Data

(63) Continuation of application No. 11/027,491, filed on Dec. 29, 2004, now Pat. No. 7,311,679, which is a continuation-in-part of application No. 10/750,369, filed on Dec. 30, 2003, now abandoned.

(51) Int. Cl.
*A61H 1/00* (2006.01)
(52) U.S. Cl. ............... 601/2; 600/439; 600/459; 601/3
(58) Field of Classification Search ............. 600/439, 600/459; 601/2–4; 606/1
See application file for complete search history.

(56) References Cited

U.S. PATENT DOCUMENTS

| | | | |
|---|---|---|---|
| 4,002,221 A | 1/1977 | Buchalter |
| 4,059,098 A | 11/1977 | Murdock |
| 4,211,949 A | 7/1980 | Brisken et al. |
| 4,291,578 A | 9/1981 | Hetz et al. |
| 4,326,418 A | 4/1982 | Pell, Jr. |
| 4,368,410 A | 1/1983 | Hance et al. |
| 4,437,033 A | 3/1984 | Diepers |
| 4,459,854 A | 7/1984 | Richardson et al. |
| 4,501,557 A | 2/1985 | Tamura et al. |
| 4,556,066 A | 12/1985 | Semrow |
| 4,567,895 A | 2/1986 | Putzke |
| 4,579,123 A | 4/1986 | Chen et al. |

(Continued)

FOREIGN PATENT DOCUMENTS

GB        820814        9/1959

(Continued)

OTHER PUBLICATIONS

Ayme et al., "Occurance of transient cavitation in pulsed swatooth ultrasonic fields", *J. Acoust. Soc. Am.* (1988) 84(5):1598-1605.

(Continued)

*Primary Examiner* — Eric F Winakur
*Assistant Examiner* — Vani Gupta
(74) *Attorney, Agent, or Firm* — Kilpatrick Townsend & Stockton LLP

(57) ABSTRACT

A transducer seal designed to seal an open aperture of a transducer housing for a therapeutic ultrasound procedure. The seal has a membrane, a retainer and a mating device for locking in place with the transducer housing. The membrane is essentially transparent to ultrasound energy while being stretched taut about the retainer. The transducer seal may be made in a disposable or re-usable form.

11 Claims, 3 Drawing Sheets

U.S. PATENT DOCUMENTS

| | | | |
|---|---|---|---|
| 4,586,512 A | 5/1986 | Do-huu et al. | |
| 4,593,699 A | 6/1986 | Poncy et al. | |
| 4,815,470 A | 3/1989 | Curtis et al. | |
| 4,865,042 A | 9/1989 | Umemura et al. | |
| 4,936,303 A | 6/1990 | Detwiler et al. | |
| 4,955,365 A | 9/1990 | Fry et al. | |
| 4,960,107 A | 10/1990 | Aida et al. | |
| 5,095,907 A | 3/1992 | Kudo et al. | |
| 5,259,383 A | 11/1993 | Holstein et al. | |
| 5,301,660 A | 4/1994 | Rattner | |
| 5,352,301 A | 10/1994 | Panchanathan et al. | |
| 5,382,286 A | 1/1995 | Fanning et al. | |
| 5,419,327 A | 5/1995 | Rohwedder et al. | |
| 5,434,208 A | 7/1995 | Batelaan et al. | |
| 5,476,438 A | 12/1995 | Edrich et al. | |
| 5,477,736 A | 12/1995 | Lorraine | |
| 5,479,930 A | 1/1996 | Gruner et al. | |
| 5,494,038 A | 2/1996 | Wang et al. | |
| 5,505,206 A | 4/1996 | Walloch | |
| 5,526,815 A | 6/1996 | Granz et al. | |
| 5,568,810 A | 10/1996 | Hamers et al. | |
| 5,623,928 A | 4/1997 | Wright et al. | |
| 5,626,554 A | 5/1997 | Ryaby et al. | |
| 5,655,539 A | 8/1997 | Wang et al. | |
| 5,669,150 A | 9/1997 | Guertin et al. | |
| 5,676,159 A | 10/1997 | Navis | |
| 5,718,228 A | 2/1998 | Hiruta et al. | |
| 5,738,098 A | 4/1998 | Brock-Fisher et al. | |
| 5,738,635 A | 4/1998 | Chapelon et al. | |
| 5,755,753 A | 5/1998 | Knowlton | |
| 5,762,066 A | 6/1998 | Law et al. | |
| 5,769,790 A | 6/1998 | Watkins et al. | |
| 5,820,623 A | 10/1998 | Ng | |
| 5,871,446 A | 2/1999 | Wilk | |
| 5,938,608 A | 8/1999 | Bieger et al. | |
| 5,938,922 A | 8/1999 | Fulk, Jr. et al. | |
| 6,027,449 A | 2/2000 | Mazess et al. | |
| 6,039,689 A | 3/2000 | Lizzi | |
| 6,039,694 A | 3/2000 | Larson et al. | |
| 6,085,749 A | 7/2000 | Wardle et al. | |
| 6,113,546 A | 9/2000 | Suorsa et al. | |
| 6,113,558 A | 9/2000 | Rosenschein et al. | |
| 6,132,378 A | 10/2000 | Marino | |
| 6,142,748 A | 11/2000 | Harris et al. | |
| 6,152,137 A | 11/2000 | Schwartz et al. | |
| 6,176,840 B1 | 1/2001 | Nishimura et al. | |
| 6,217,515 B1 | 4/2001 | Yamakawa et al. | |
| 6,233,476 B1 | 5/2001 | Strommer et al. | |
| 6,261,249 B1 | 7/2001 | Talish et al. | |
| 6,264,605 B1 | 7/2001 | Scirica et al. | |
| 6,270,460 B1 | 8/2001 | McCartan et al. | |
| 6,302,848 B1 | 10/2001 | Larson et al. | |
| 6,306,146 B1 | 10/2001 | Dinkler | |
| 6,366,831 B1 | 4/2002 | Raab | |
| 6,419,648 B1 | 7/2002 | Vitek et al. | |
| 6,423,077 B2 | 7/2002 | Carol et al. | |
| 6,488,639 B1 | 12/2002 | Ribault et al. | |
| 6,506,171 B1 | 1/2003 | Vitek et al. | |
| 6,554,826 B1 | 4/2003 | Deardorff | |
| 6,561,389 B1 | 5/2003 | Earle | |
| 6,575,906 B1 | 6/2003 | Schembri, Jr. et al. | |
| 6,607,498 B2 | 8/2003 | Eshel | |
| 6,613,004 B1 | 9/2003 | Vitek et al. | |
| 6,618,620 B1 | 9/2003 | Freundlich et al. | |
| 7,311,679 B2 * | 12/2007 | Desilets et al. | 601/3 |
| 2002/0128592 A1 | 9/2002 | Eshel | |
| 2003/0083536 A1 | 5/2003 | Eshel et al. | |

FOREIGN PATENT DOCUMENTS

| | | |
|---|---|---|
| JP | 57-191521 | 11/1982 |
| JP | 3-275044 | 12/1991 |

OTHER PUBLICATIONS

Clarke et al., "Physical and chemical aspects of ultrasonic disruption of cells", *J. Acoust. Soc. Am.* (1970) 47(2):649-653.

Flynn et al., A mechanism for the generation of cavitation maxima by pulsed ultrasound *J. Acoust. Soc. Am.* (1984) 76(2):505-512.

Fry et al., "Threshold ultrasonic dosages for structural changes in the mammalian brain", *J. Acoust. Soc. Am.* (1970) 48(6):1413-1417.

Kinney, "Body contouring with external ultrasound", *Plastic & Reconstruct. Surg.* (1999) 103:728-729.

Padmaker, "Thresholds and mechanisms of ultrasonic damage to 'organized' animal tissues", *Symposium on Biological Effects and Characterizations of Ultrasound Sources* (1977) Hazzard et al., Eds., pp. 224-239.

Supplemental European Search Report directed to Application No. EP 0481606 (completed May 25, 2010).

* cited by examiner

DISPOSABLE TRANSDUCER SEAL

CROSS-REFERENCES TO RELATED APPLICATIONS

The present application is a continuation of U.S. application Ser. No. 11/027,491, filed Dec. 29, 2004, which is a continuation-in-part of U.S. patent application Ser. No. 10/750,369, filed Dec. 30, 2003 (now abandoned) entitled "Disposable Transducer Seal", and related to that of the following applications each of which was filed on 30 Dec. 2003: 10/750,370, entitled "Medical Device Inline Degasser" (now abandoned); 10/751,344, entitled "Articulating Arm for Medical Procedures"; 60/533,528, entitled "Position Tracking Device"; 60/534,036, entitled "Ultrasound Therapy Head with Movement Control"; 60/533,958, entitled "Systems and Methods for the Destruction of Adipose Tissue"; 60/534,034, entitled "Component Ultrasound Transducer"; the full disclosure of each of these applications are incorporated herein by reference.

BACKGROUND OF THE INVENTION

1. Field of the Invention

The present invention pertains to a sealing device for retaining a coupling fluid such as degassed water within an ultrasound transducer housing.

2. Description of the Prior Art

Ultrasound transducers require a coupling medium to connect the transducer to a patient in order to minimize the reflection and refraction of ultrasound waves when those waves cross a border between two materials of similar acoustic properties. One of the biggest issues in coupling transducers to a patient either for a diagnostic ultrasound device, or a therapeutic ultrasound device, is the presence of air. Coupling agents are used to eliminate air bubbles between the transducer and the patient. For diagnostic purposes, mineral oils, hydro-gels and even water can be used to couple a transducer to a patient. In therapeutic procedures the coupling agent should be more strictly controlled so that even minute air bubbles are eliminated.

In high intensity focused ultrasound (HIFU) procedures the need to couple the transducer to the patient often includes a means of cooling the face of the transducer, or cooling a patient's skin, with a medium that will pass ultrasound energy with little or no attenuation or adverse effect. Typically this medium is water, sometimes with antibacterial additives, held within a transmission cavity with a cap or membrane, and through which the ultrasound energy passes.

One major issue with such a system arises from bubble formation caused by dissolved gasses being drawn out of solution. These bubbles provide an impedance mismatch to the ultrasound energy, causing scattering and localized heating, leading to observed effects such as reduced effectiveness of therapy, the destruction of the cap or seal, or patient hyperemia.

Atmospheric water for example, contains approximately 8.5 PPM (parts per million) $O_2$, and 14.5 PPM $N_2$ as well as other dissolved gasses. Using dissolved oxygen (DO) as an indicator, it is possible to determine the relative contents of other gasses, $CO_2$, CO, $N_2$, etc... This can be done using the partial pressure values of the other gases. Reducing the concentration of DO (and other gases) inhibits the incidence of cavitation. However for high intensity focused ultrasound (HIFU) procedures, the optimal dissolved gas content is highly dependent on the treatment being performed, and the type of ultrasound instruments being utilized. To date, we are aware of no treatise clearly defining the operable boundaries of DO and other dissolved gases in HIFU operations.

The common method used by the industry is to prepare the fluid by passing it through a filtration and de-ionization process to remove impurities and particulates that may precipitate out, contaminate or provide nucleation sites for bubbles. The coupling fluid is then degassed to some minimum level before introduced into the system. Typically degassing is performed by bulk cavitation under a vacuum or boiling at atmospheric or sub atmospheric pressure and then sealing the degassed fluid in a container.

In a completely sealed system the dissolved gas content will remain constant, but as described below the gas content will strive to meet equilibrium with the partial pressure of the local atmospheric conditions. During short procedures or low power ultrasound procedures the re-gas rate is usually slow enough not to cause problems. In longer procedures and/or at higher powers, the probability that re-dissolved gas will be drawn into the fluid, and subsequently interfere with ultrasound transmission, goes up considerably since it is impossible to prevent gas diffusing through the system lining, joints and seals without investing in prohibitively expensive parts and materials.

The methods by which gasses come out of solution or enter the cooling system are various, some examples of the more common range from pressure changes within the cooling system caused by physical restriction to atmospheric conditions. Local pressure changes such as rectified diffusion from HIFU or temperature changes will bring gas out of solution as will displacement of the partial pressure of one gas by another, or by material leaching. Other methods by which gas may enter the system include diffusion through the tubing, seals and structure of the cooling system in the same way a balloon deflates, trapping micro bubbles within the surface structure and pockets of the cooling system, chemical reactions between materials in the cooling system, or as a by product of bacterial growth within the cooling system.

Precautions such as using low permeability materials for the tubing are regularly employed, but even with such precautions, the re-gas rate can become a major issue. Other methods used to reduce the effects of re-gassing include the introduction of surfactants or wetting agents to prevent bubble formation, using larger volumes of fluids, and the use of hydrophilic and/or hydrophobic polymers such as polyvinylpyrolidone (PVP). Experimental testing has shown these provide only a short term solution.

Numerous examples in the prior art show differing solutions to the problems of dealing with coupling HIFU transducers to a patient as well as providing an apparatus for degassing a fluid. However there has been thus far nothing demonstrating the feasibility or utility of an in line degassing mechanism combined with a HIFU therapy system during an actual medical procedure or application. The use of an inline degasser during a procedure mandates the use of a transducer housing having a cavity where the cooling/coupling fluid may circulate around the transducer. To prevent the coupling fluid from escaping the cavity and to minimize gas from entering the cavity, a seal is needed.

The inability of the prior art to maintain a controlled dissolved gas content in a cooling fluid over a prolonged procedure acts as a forced limitation to prolonged HIFU therapy.

Thus there remains a need for a seal capable of retaining a degassed coupling fluid for use in a HIFU procedure within a cavity containing a HIFU transducer.

BRIEF SUMMARY OF THE INVENTION

It is an objective of the present invention to provide for a seal that is both inexpensive to manufacture, and that can be quickly and easily installed into a transducer housing.

It is a further object of the invention to make a seal that is disposable so reuse and re-sterilization concerns can be avoided.

These objectives are provided for in a disposable transducer seal comprising a membrane being substantially transparent to ultrasound energy, the membrane being non-porous to water and acoustic coupling fluids; a retainer having a substantially annular configuration for holding the membrane, and a means for mating the retainer with a transducer housing.

In an alternative embodiment, there is an apparatus for maintaining a barrier between a transducer housing and an outside environment. The apparatus comprising a membrane being substantially transparent to ultrasound energy and a means for sealing the membrane to the transducer housing wherein the sealing means provides for a substantially fluid tight barrier between the transducer housing and the outside environment.

In another embodiment there is a method of preparing an ultrasound transducer housing having a coupling fluid chamber for use. The method comprising the steps of (a) preparing an ultrasound transducer housing for receiving a coupling fluid; (b) engaging a transducer sealing device to the ultrasound transducer housing such that the coupling fluid chamber is sealed, and (c) filling the chamber with a coupling fluid.

There is still further a method of making a transducer sealing device, the method comprising the steps of: (a) forming a retainer having an engaging fitting element; (b) placing an acoustically transparent material across the retainer; and (c) securing the material to the retainer.

There is still another method of sealing a transducer housing using a transducer sealing device, the method comprising the steps of: (a) forming an acoustically transparent material into a shape for fittingly engaging a transducer housing having a fluid chamber; and (b) securing the shape to the transducer housing such that the fluid chamber is substantially sealed.

DETAILED DESCRIPTION OF THE INVENTION

Figure 1A:
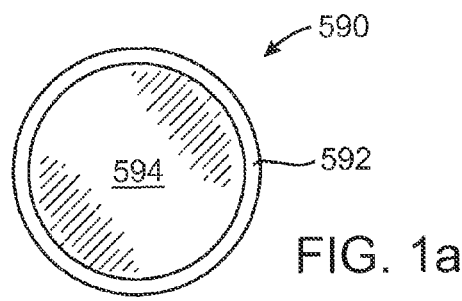
FIGS. 1A-C show three configurations of a transducer sealing device.

The device of the present invention is a disposable transducer seal (seal). The seal is designed for use with a HIFU therapy system for cosmetic applications, such as the reduction or ablation of adipose tissue. The seal comprises a membrane, a retainer and a means for attaching the seal to a transducer housing. The transducer housing is shaped similar to an inverted cup having a gap space for a coupling fluid such as degassed water. The seal is used to retain the degassed water in the gap space without the water spilling onto a patient during an ultrasound procedure. The seal is intended to provide both an air tight seal, and a barrier to prevent cross contamination of the different fluids on opposite sides of the membrane.

More specifically, in one embodiment, there is a disposable transducer seal comprising a membrane being substantially transparent to ultrasound energy, the membrane being non-porous to water and acoustic coupling fluids. A retainer having a substantially annular configuration is used for holding the membrane, and there is a means for mating the retainer with a transducer housing.

In another embodiment, there is an apparatus for maintaining a barrier between a transducer housing and an outside environment. The apparatus comprising a membrane being substantially transparent to ultrasound energy, and a means for sealing the membrane to the transducer housing wherein the sealing means provides for a substantially fluid tight barrier between the transducer housing and the outside environment.

The membrane used must be suitable for use with an ultrasound transducer, while simultaneously providing a non-porous barrier between the coupling fluid used within a transducer housing, and the environment outside. Numerous materials are usable for a membrane, and in general we have found the membrane properties must provide the necessary level of acoustic transparency combined with the ability to prevent air diffusion into the coupling fluid. The presence of dissolved gasses in a coupling fluid can adversely affect HIFU therapy.

Standing water may contain high levels of dissolved gases. We measured dissolved oxygen (DO) content of tap water left to stand at room temperature for several hours and found levels that produced high levels of cavitation when used as a coupling fluid for a HIFU ultrasound system. By degassing the coupling fluid, the incidence of cavitation can be greatly reduced. We have found that when DO levels are reduced below 5 parts per million (PPM), the incidence of cavitation is greatly reduced. Furthermore we have found that by chilling the coupling fluid, the incidence of cavitation can be further controlled. Optimally we have observed that where DO levels drop to less than 2 PPM, cavitation, along with its detrimental effects (such as hyperemia, the burning of the patient skin due to energy focused in the coupling fluid instead of the ultrasound transducer focal zone), are almost completely absent from the coupling fluid.

Therefore it is highly desirable that the membrane have sufficient integrity to prevent the diffusion of gasses across the membrane, such that the coupling fluid maintains a DO content of 5 PPM or less. The membrane may be somewhat porous to gas if there is a degassing system used in conjunction with the coupling fluid. However, it would still be necessary for the membrane to be sufficiently robust to prevent gas diffusion into the coupling solution at a rate faster than the degassing system can remove it.

The membrane is composed of a compound or material being essentially or substantially transparent to ultrasound energy. Acoustic transparency can be determined for a material through computer simulation or experimentation. We measured intensity levels dropping 1 dB or less with the introduction of a 50 micron thick polyimide membrane. The membrane may be composed of naturally occurring materials such as latex rubber, or a synthetic material like a thin film plastic or synthetic rubber. Uniformity in the membrane of the seal is desirable as it reduces the detrimental effects on the ultrasound beam during a procedure. A thermoforming polyimide can readily be formed into a desired shape and provides a good example of a material that can be used for a membrane. For manufacturing considerations and for optimal performance, the synthetic polyimide is preferred. The membrane may be flexible or inflexible as long as it is drawn taut about the retainer. (While the membrane may be inflexible, it is preferred the membrane be a little flexible so that it can conform to the curves of a patients body more readily.) Some flexibility also allows the membrane to respond to fluid pressure changes during procedures. This responsiveness during a procedure helps maintain a constant pressure environment for the fluid, since the membrane may expand a little or contract a little due to variations in pressure in the system. The membrane serves as an acoustic window, so it is desirable that the membrane is substantially transparent to ultrasound energy. Smoothness in its surfaces during manufacturing will help reduce signal scattering, reflection or attenuation, thus improving performance of the membrane. A membrane having desirable acoustic properties is required. If the membrane is thermo-formable, it allows for easier manufacturing of the membrane. The membrane is preferably made a uniform thickness, so as to reduce signal scattering or other loss of the ultrasound signal passing through the membrane. The membrane described above is merely illustrative and many other possible materials and methods could be used without departing from the spirit of the present invention.

The retainer may be assembled from any material. However since the retainer may be in direct contact with the patient, it is preferred to be made of a material that is easily formable (such as an extruded plastic, or moldable plastic) so that the sealing device may be discarded after a single use. The membrane is drawn taut over the retainer, or drawn taut and the retainer is placed down about the membrane so that the membrane remains taut during a medical procedure. Alternatively the membrane may be made of a material highly resistant to cleaning solutions (e.g. disinfectant solvents) or cleaning procedures (e.g. autoclave), so the transducer seal may be cleaned and reused a number of times. However because high intensity ultrasound has adverse effects on materials used in the membrane component of the transducer seal, ultimately a material having high acoustic transparency also lacks sufficient stability to be "permanent" or "non-disposable" device, and after a limited number of uses, even a resistant or robust transducer sealing device, will necessarily be discarded.

The seal has a means for mating with a transducer housing. The means may be such as the retainer is shaped as an interlocking ring with the transducer housing having a conforming receiving aperture or shape. Or the transducer housing may have clips for latching on to tabs on the retainer. Other means of mating to the transducer include a magnetic lock, a screw-in pin, a temporary adhesive, an interference fitting male and female part (one being on the retainer, the corresponding part on the transducer housing). The principle concern is to reduce the leakage of fluid and gas across the membrane and/or the retainer to preserve the operating environment of the transducer.

The retainer may also include a means for identifying the sealing device to the transducer housing, or its attached ultrasound system. The means may be an electronic device such as an encoded chip or flex circuit, or it may be linked to the mating means, such that if the mating is not properly done the transducer housing and corresponding ultrasound system will not recognize the retainer and therefore remain in a safe mode. Use of an electronic device further provides for the means to encode additional information into the chip or circuit. For instance the life of the membrane may be such that it should not be used for more than a certain about of time, or for more than a certain number of active HIFU transmissions. The circuit or chip may have a digital counter that can be read, or written to, by the therapy head. In this case the membrane can be programmed with a "usable life" which if exceeded, would cause the chip to no longer be recognized by the therapy head or main system, and require the user to change the membrane or retainer for safety purposes.

The recognition means may be a visually recognizable color code for matching colors and/or patterns of the transducer sealing device to a therapy head. The means may be a unique type of mechanical connection as simple as a customized thread of the retainer and therapy head screw connection, an impedance detecting circuit or a safety device that prohibits the therapy head from operating without the proper retainer in place. The detection means may also be imprinted into the membrane component in the form of a chemically or optically detectable dopant.

Either the membrane or the retainer may also have a clear window. The window is a small gap space designed to correspond to the location of an optical emitter and photo-optical receiver such that an acoustic gel having a safety dopant can be detected by the transducer housing or ultrasound system through the sealing device.

Although the principle embodiment is for the entire transducer sealing device to be disposable to facilitate the quick changing of the seal, other variations and reuse combinations are well within the spirit of the present invention. If a membrane material can be cleaned and reused indefinitely, it would not be necessary to discard the membrane after each use. However during the course of our experimentation and computer modeling, we have not found such a material. We have found membrane materials that may be reused due to their resilience to cleaning solutions and high intensity focused ultrasound energies. But ultimately these materials break down, lose uniformity of their surfaces, and become unacceptably porous to gas and fluid.

One variation is to provide either a shaped or flat membrane that may be handled by an operator as an individual component which is held in place over a transducer housing using a reusable sealing means. Such means may be a screw like cap, a snap fitting piece, an interference fitting piece, O-ring or even the stretch tension of the membrane itself, assuming it is precisely shaped to the transducer housing. Any manner of removably joining the membrane to the housing would be acceptable.

The sealing device may be made using a variety of methods. One example is to form a retainer having an engaging fitting element for securing itself to the transducer housing. An acoustically transparent material is placed across the retainer and then secured to it. The retainer has a window or aperture through which acoustic energy can pass.

A second example is to form an acoustically transparent material into a shape for fittingly engaging the transducer housing and then securing the shape to the housing.

The transducer housing can be prepared for receiving the sealing device in numerous manners. The preferred embodiment of preparing the transducer housing is to make sure the housing is ready to receive a new sealing device. If there is an old sealing device in place, the fluid should be drained from it, then the housing can be inverted so the sealing aperture faces up. An old seal may be removed and a new one placed on the housing. If the housing is already clean and dry, then the sealing device need only be placed over the acoustic window and secured in place.

Figure 1B:
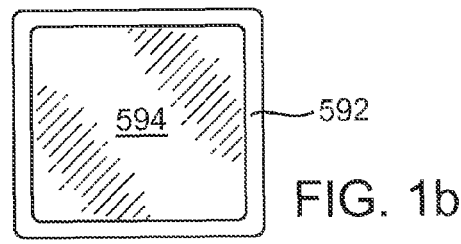
Figure 1C:
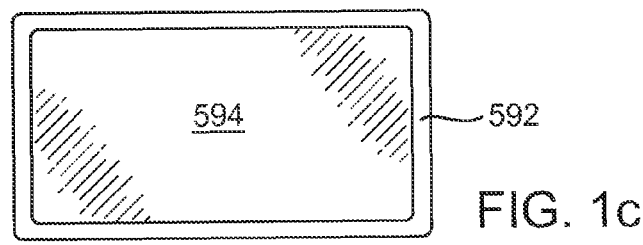

Referring now to the drawings, FIG. 1 illustrates several possible designs. The retainer 592 of the disposable transducer seal 590 has an annular configuration. The membrane 594 is drawn tightly around the retainer 592. Regardless of the material construction of the membrane, it is necessary for the membrane to be drawn tightly about the retainer and held in place. Thus if the membrane is a polymer formed into a thin layer, or a softer latex rubber, the retainer serves to maintain the shape and rigidity of the membrane during use. If the membrane is a softer material, such as a latex rubber, then the retainer serves to keep the membrane taut. Preferably the membrane has no slack in it, so there is no play or deformation of the membrane during use. A limited amount of deformity is desirable so the membrane can flex slightly to be concave or convex relative to the transducer. However ripples in the membrane material, folds or even a somewhat flimsy shape to the membrane may have adverse effects on the transmission of ultrasound energy during a procedure. The configuration is a circular ring, square, rectangle or other shape as may provide the best matching of the therapy head mouth to the transducer sealing device. Thus the annular configuration depends on the aperture of the transducer housing the seal must mate with. The precise shape will vary from one transducer housing to another. The shapes shown are merely illustrative and not to be taken as limiting in any sense. Many shapes are possible, but the preferred embodiment is a substantially annular ring.

Figure 2A:
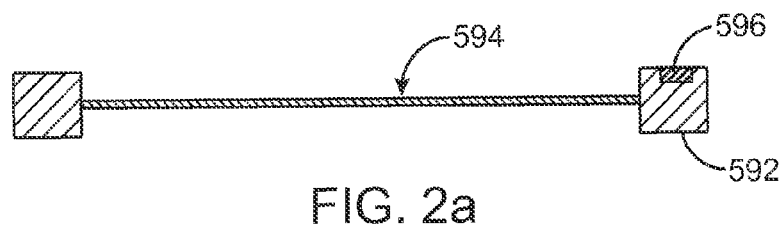
FIGS. 2A-C show cross-section views of the transducer sealing device.
Figure 2B:
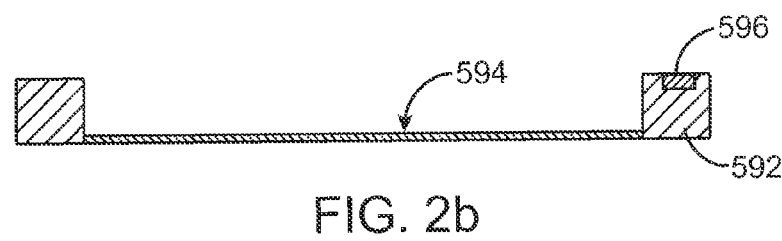
Figure 2C:
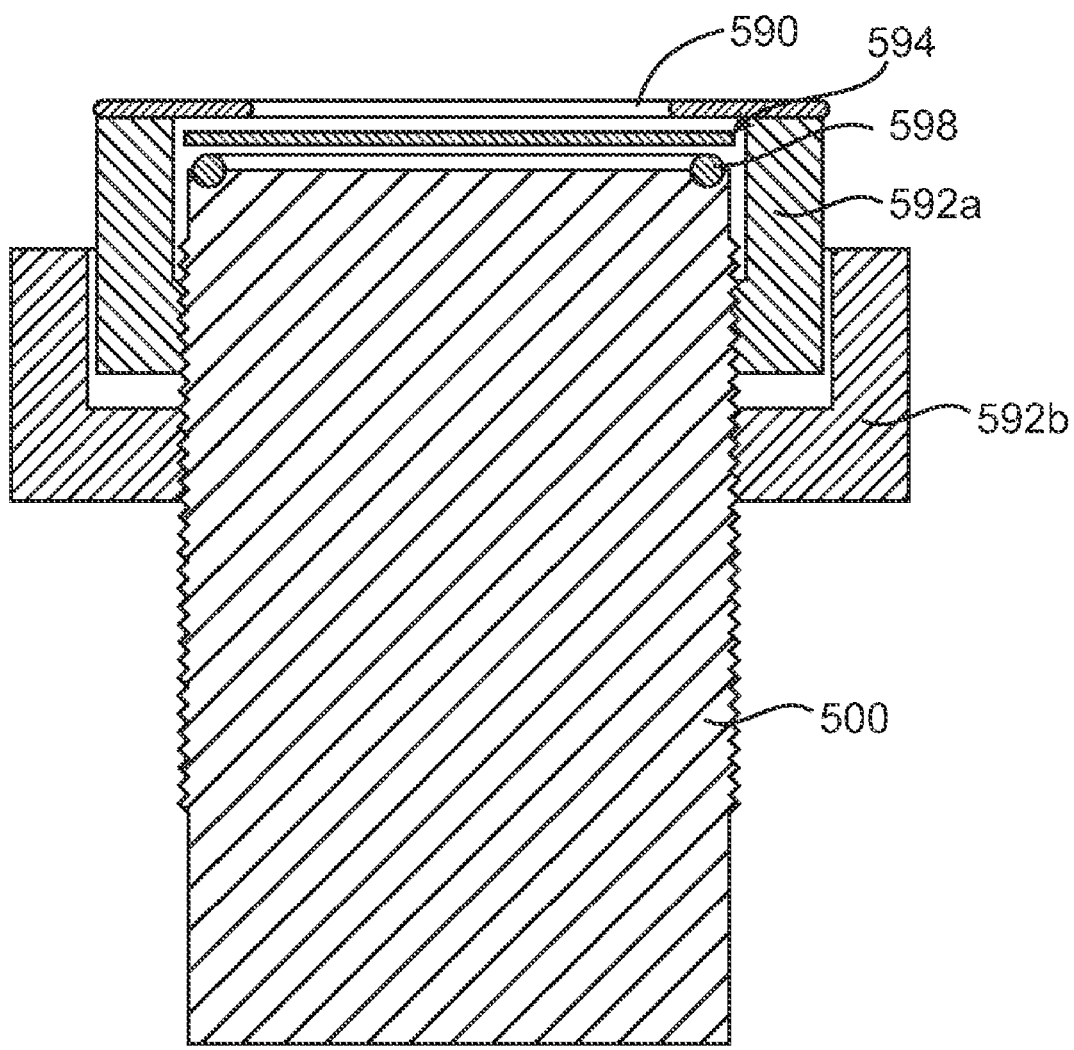

FIG. 2 illustrates a cross section of the sealing device. As can be seen the membrane is drawn tightly either within the retainer (FIG. 2A) or across the surface face of the retainer (2B). Optional elements include the encoder chip 596 illustrated in both drawings. FIG. 2C illustrates the transducer head with a membrane 594 held in place by a pair of threaded retainers 592a, 592b. An O-ring 598 between the membrane and the transducer housing 500 provides a fluid seal between the membrane and the transducer housing. Note: the drawing is not to scale, there are no gap spaces between the parts as shown in the illustration.

Figure 3:
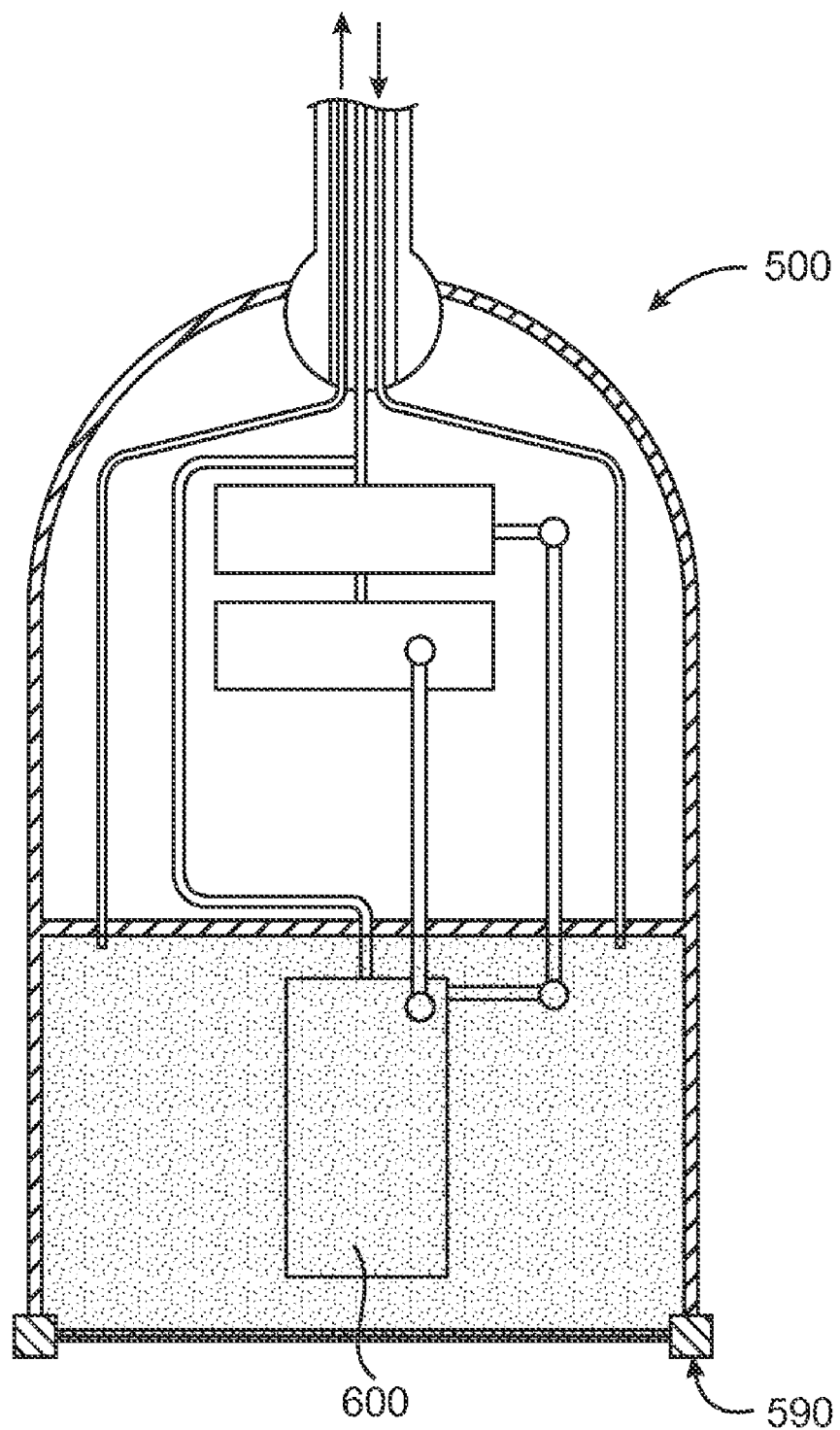
FIG. 3 illustrates a cut away view of a transducer sealing device on a transducer.

FIG. 3 illustrates the mating of the seal 590 to a transducer housing 500. The housing is shaped similar to an inverted cup containing an electronics and motor assembly for moving and controlling the transducer and any additional electronic components that may be integrated into the housing. The seal 590 is placed over an open aperture on the transducer housing. The design of the transducer housing is such that the transducer is placed aperture end toward the patient, and the transducer can abut the skin of the patient. The seal is needed to prevent the degassed water from leaking out, and to prevent air from leaking in.

The seal is mated to the transducer housing. The mating means may be any number of mechanical connections that allow for the air and water tight seal described above. Once the seal is in place, the cavity in the transducer housing may be flooded with a coupling fluid without the fluid escaping. The seal may also have an electronic or mechanical recognition device such that the transducer housing will recognize the proper placement of the seal and move the ultrasound machine from a safe mode to an active mode. Furthermore an optical window may be placed either in the membrane or in the retainer so that any kind of optical sensor or safety device using an optical sensor may still detect the proper safety material across the seal. Alternatively the membrane itself is optically transparent, or transparent to selected wavelengths of visible light.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

What is claimed is:

1. A HIFU therapy apparatus comprising:
a cup shaped housing having an aperture;
a motor assembly positioned within said housing;
a HIFU transducer positioned within the housing such that the transducer is aligned in said cup shaped housing to direct ultrasound energy through said aperture, said transducer being movable through said motor assembly;
a seal having a taut membrane substantially transparent to ultrasound energy and having a retainer for holding the taut membrane in a desired shape, the seal being releasably engaged to the housing and covering the aperture so as to form a water tight connection between the seal and the housing; and
a recognition device for determining the proper placement of the seal relative to the cup shaped housing, the recognition device acting as a safety lock to prevent the transducer from operating until the seal and the housing are properly engaged.

2. A HIFU therapy apparatus as in claim 1, further comprising a plurality of electronic control elements positioned within the housing.

3. A HIFU therapy apparatus as in claim 2, wherein the electronic control elements are connected to the motor assembly to operate and move transducer within the housing.

4. A HIFU therapy apparatus as in claim 1, wherein the seal is maintained when the cup shaped housing is inverted.

5. A HIFU therapy apparatus as in claim 1, wherein the membrane is a thermo-formable polyimide.

6. A HIFU therapy apparatus as in claim 1, wherein said membrane is resistant to cleaning solutions and/or cleaning procedures.

7. A HIFU therapy apparatus as in claim 1, wherein the recognition device comprises a visually recognizable color code for matching colors and/or patterns of the transducer seal to cup-shaped housing.

8. A HIFU therapy apparatus as in claim 1, wherein the recognition device comprises a customized screw thread between the housing and seal.

9. A HIFU therapy apparatus as in claim 1, wherein the recognition device comprises an impedance detecting circuit.

10. A HIFU therapy apparatus as in claim 1, wherein the recognition device comprises a safety device that prohibits the therapy head from operating without the proper seal in place.

11. A HIFU therapy apparatus as in claim 1, wherein the recognition device comprises a chemically or optically detectable dopant.

\* \* \* \* \*